United States Patent [19]

Bell

[11] Patent Number: 5,134,996
[45] Date of Patent: Aug. 4, 1992

[54] INSPIRATION AND EXPIRATION INDICATOR FOR A SUCTION CATHETER

[75] Inventor: Craig J. Bell, Winchester, N.H.

[73] Assignee: Smiths Industries Medical Systems, Inc., Keene, N.H.

[21] Appl. No.: 641,717

[22] Filed: Jan. 9, 1991

[51] Int. Cl.$^5$ .......................... A62B 9/06; A62B 7/00; A61M 16/00; A61M 5/32

[52] U.S. Cl. .......................... 128/207.14; 128/205.23; 604/163; 604/171

[58] Field of Search ........................ 128/207.14, 207.15, 128/207.16, 200.26, 205.19, 205.12, 911, 912, 205.23, 204.23; 604/267, 268, 118, 119, 163, 171, 173

[56] References Cited

U.S. PATENT DOCUMENTS

| | | | |
|---|---|---|---|
| 2,904,033 | 9/1959 | Shane | 128/205.23 |
| 3,991,762 | 11/1976 | Radford | 128/207.16 |
| 4,638,539 | 1/1987 | Palmer | 604/171 |
| 4,832,015 | 5/1989 | Nowacki et al. | 128/205.23 |
| 4,850,350 | 7/1989 | Jackson | 604/171 |
| 5,029,580 | 7/1991 | Radford et al. | 128/207.14 |
| 5,065,754 | 11/1991 | Jensen | 128/207.14 |
| 5,083,561 | 1/1992 | Russo | 128/207.14 |
| 5,088,486 | 2/1992 | Jinotti | 128/207.14 |

FOREIGN PATENT DOCUMENTS

| | | | |
|---|---|---|---|
| 92705 | 2/1962 | Denmark | 128/205.19 |
| 3325797 | 1/1985 | Fed. Rep. of Germany | 128/207.15 |

Primary Examiner—Edgar S. Burr
Assistant Examiner—Kimberly L. Asher
Attorney, Agent, or Firm—Sewall P. Bronstein; Robert M. Asher; Dike, Bronstein, Roberts & Cushman

[57] ABSTRACT

A vent cycle indicator for a suction catheter formed by a sleeve connected between a collar having a wiper seal and a crosspiece. The suction catheter includes a vacuum connection member having a normally closed valve. A catheter tube is connected to the vacuum connection member and extends through the collar and crosspiece. The crosspiece is for connection to a ventilator such that during ventilation the indicator sleeve expands and contracts during the inspiration and expiration cycles. The protective sleeve may be provided between the collar and the vacuum connection member to keep the catheter tube enclosed.

4 Claims, 2 Drawing Sheets

INSPIRATION AND EXPIRATION INDICATOR FOR A SUCTION CATHETER

BACKGROUND OF THE INVENTION

The present invention is directed to a suction catheter for use in removing undesirable fluid from a patient.

A number of commercially available devices are currently in use for the purpose of ventilating a patient. Use of traditional endotracheal tubes for such purpose is quite satisfactory. However, during patient ventilation, frequently fluids accumulate in the trachea and bronchi Commonly, mucous secretions and other fluids accumulate along the interbated pathway below and within the vicinity of, for instance, an inflated cuff, when employed. The patient may try to swallow the secretions, causing muscle contractions and tissue movement around the endotracheal tube, thereby contributing to the discomfort that is present during intubation. The accumulation of these fluids also can inhibit ventilation and increase the risk of infection. Accordingly, it is necessary for the accumulated fluids to be aspirated or suctioned from the patient.

In the past, suctioning has been achieved by removing the ventilation equipment thereby interrupting the patient's assisted ventilation and inserting a catheter connected to a vacuum source into the trachea and brochi. After the fluid is removed via the catheter by application of the vacuum, the ventilation equipment is reattached to the patient and the ventilation is resumed.

More recently, suction catheters have been provided which may be used simultaneously with ventilation equipment. Closed ventilation suction catheter systems such as that available under the trade designation of STERICATH, Model No. 6100 available from Smiths Industries Medical Systems, Inc., the assignee of the present invention, have now come into wide use. This ventilation suction catheter system includes a catheter tube, a crosspiece connecting member for connecting to an endotracheal tube and also for connection to a ventilating apparatus, a means for connecting a vacuum located at the end opposite to that nearest the patient, a control valve to control the suction and a protective sleeve located betewen the crosspiece and the control valve. The closed ventilation suction catheter systems make it possible to continue the ventilation while at the same time applying suction to remove undesired accumulated fluid from a patient.

It is highly desirable for personnel supervising a patient on a closed ventilation system to know as soon as possible if a problem should arise. A ventilator normally has several alarms set up for a pressure range or a volume range. It is an object of the present invention to provide an additional safeguard in the form of an immediate visual indication of ventilation within clear sight of the patient. Should respiration be interrupted, the supervising personnel would visually notice this disruption without any undue delay, permitting remedial operations to commence.

SUMMARY OF THE INVENTION

The present invention is directed to a suction catheter for removing undesirable fluid from a patient while providing a visual indication of patient respiration.

The suction catheter includes a catheter tube connected at its proximal end to a vacuum source. A crosspiece is mounted so as to surround the catheter tube in the vicinity of its distal end. The crosspiece provides an opening for connection to a respirator. An annular collar encircles the catheter tubes separate from the crosspiece and having a wiper seal in contact with the outer wall of the catheter tube. The catheter tube may be reciprocally moved through the collar and crosspiece into the patient. An indicator sleeve is connected between the annular collar and the crosspiece. As the patient respirates, the indicator sleeve inflates and deflates thereby providing a visible indication of the respiration. A protective sleeve is also generally provided connected between a vacuum control valve and the annular collar.

Other objects and advantages of the present invention will become apparent during the following description of the presently preferred embodiment of the invention taken in conjunction with the drawings.

DETAILED DESCRIPTION OF THE PREFERRED EMBODIMENT

Figure 1:
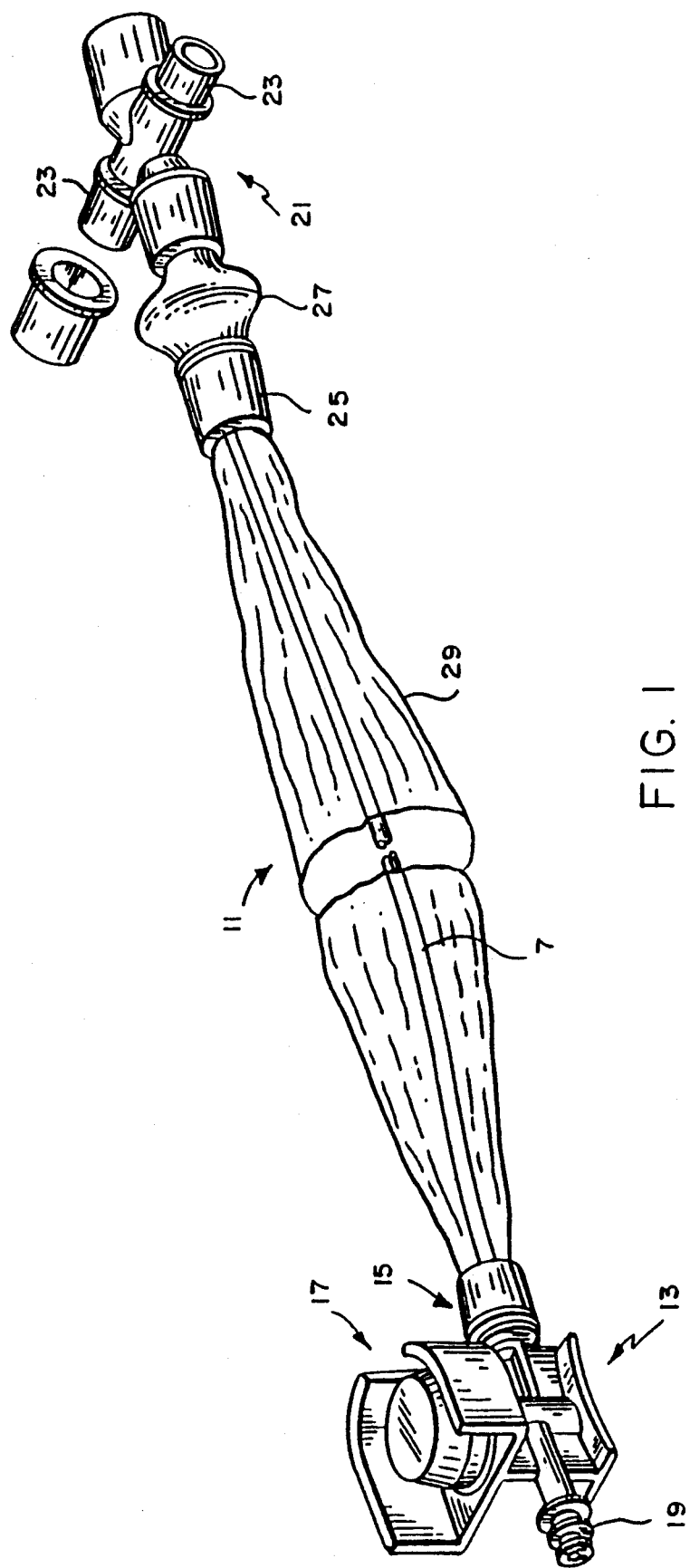
FIG. 1 is a perspective view of the suction catheter having a vent cycle indicator of the present invention.

Referring now to the drawings, FIG. 1 illustrates a suction catheter using the vent cycle indicator of the present invention. The suction catheter 11 includes a catheter tube 7. The proximal end of the catheter tube 7 is connected to a suction control member 13 The suction control member includes a collar 15, a valve 17 and a vacuum connection outlet 19. The outlet 19 is for connection to a vacuum source. The valve 17 is normally closed so as to prevent suction from reaching the catheter 7. The valve 17 includes a valve member illustrated as a spool type valve preferably made of buthyl rubber. The valve is operated by manually applying a force to the top of the valve rubber member whereby the valve member is pushed down such that it no longer blocks the passageway in the catheter tube and thereby suction can be applied through the catheter tube 7. Upon release of the manual force, the valve returns to its resting position. The rubber member is ultrasonically welded to the valve body. The suction control may be provided by other devices in place of the normally closed valve, such as an open port valve.

Down near the distal end of the catheter tube 7 there is a crosspiece 21 which surrounds the catheter tube 7. A crosspiece 21 is provided with two ports 23 which may be connected to ventilation apparatus. Ventilation ma also be provided using only a single port 23 and a Y-connector for connection to a return line and an intake line. The crosspiece 21 can be connected through a suitable connecting element to a patient. Such element being, for example, an oral and/or nasal connecting element and particularly an endotracheal or tracheostomy connector.

A vent cycle indicator is connected between the crosspiece 21 and a collar 25. An indicator sleeve 27 provides the visual indication of respiration. A protective polymeric sleeve 29 may be connected between the collar 25 and the collar 15 so as to enclose the catheter tube 7.

The catheter tube 7 may be a single lumen catheter for providing suction. However, many variations are possible for assisting with the suctioning process. The catheter tube may be provided with a second conduit which may be a second lumen in a double lumen catheter or a second catheter configured as a tube within a tube. The second lumen may be provided for the provision of irrigating fluid to lavage the patient while suctioning or the second lumen may be used for providing oxygen to the sight during the suctioning process. Alternatively, the second conduit may be used for providing oxygenated irrigating fluid to the suctioning sight. By oxygenating the irrigating fluid, the effects of oxygen desaturation are minimized. A still further alternative is to provide three conduits through the catheter tube 7. These may be provided in a number of different configurations using double lumen catheters, single lumen catheters or a single triple lumen catheter. The three conduits may be used for suctioning, lavage and oxygenation. Thus, the fluid may be provided to lavage the patient and remove debris for suctioning while the oxygen line provides oxygen to remedy the effects of oxygen desaturation caused by the suctioning.

Figure 2:
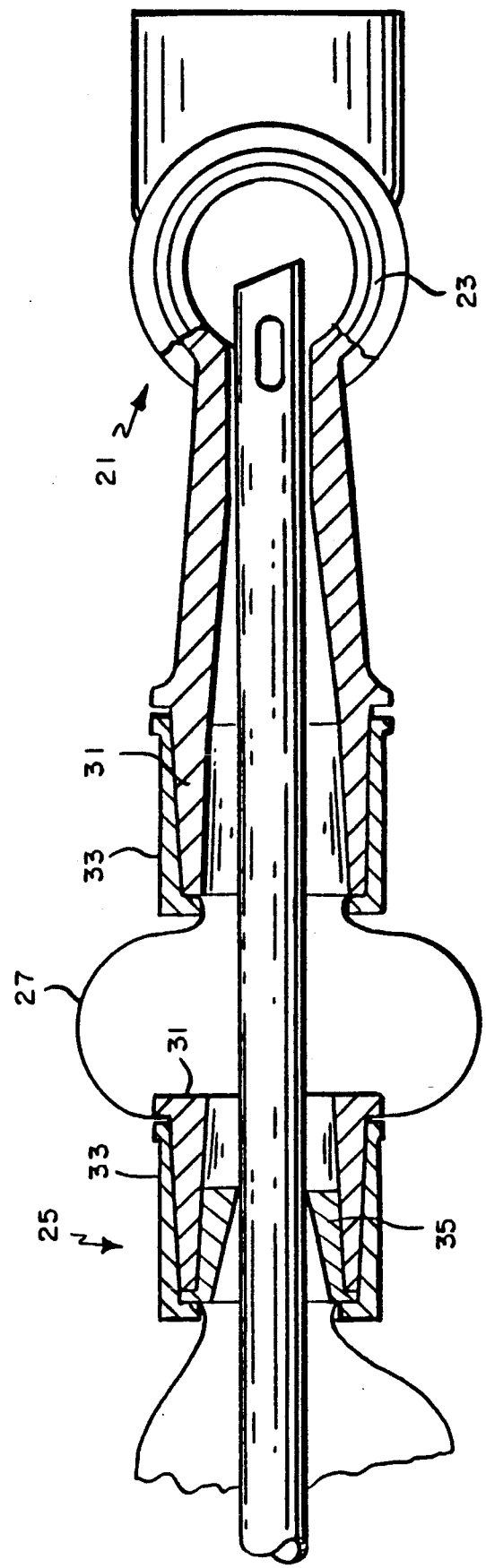
FIG. 2 is a cross sectional view of the vent cycle indicator of the present invention.

Referring now to FIG. 2, the construction of the vent cycle indicator of the present invention can be described in greater detail. The crosspiece 21 and the collar 25 are each formed with an externally threaded member 31 and an internally threaded member 33. The ends of the indicator sleeve 27 are adhesively secured between the externally threaded members 31 and the internally threaded members 33. In assembling, the internally threaded members 33 are twisted and threaded over the externally threaded members. The ends of the indicator sleeve 27 and an adhesive are located between the threaded members. A typical adhesive is polyvinylchloride doped tetrahydrofuran. The separate collar 25 is provided with a wiper seal 35. The wiper seal can be made of a silicone rubber material. The wiper seal surrounds the catheter tube 7 and provides a substantially air tight seal therebetween, yet still permits the catheter tube to move reciprocally back and forth through the collar. As air is provided into and out of the patient through the port 23 of the crosspiece, the air travels through the crosspiece 21 through the vent cycle indicator 27. Since it is blocked by the wiper seal 35, the indicator sleeve 27 is inflated when air is being provided to the patient and is deflated during the expiration cycle from the patient.

The crosspiece 21 permits air flow therethrough. It is possible to include a modified wiper on the inside diameter of the crosspiece 21 which may be used to clean the outer periphery of the catheter tube without sealing the air flow.

The indicator sleeve 27 and the protective sleeve 29 are formed of a flexible lightweight transluscent plastic material such as a high clarity polyethylene with a typical thickness of about 0.002 inches.

The vent cycle indicator of the present invention advantageously provides an immediate visual indication of the inspriration and expiration cycles experienced by a patient during ventilation.

While a preferred embodiment of the present invention has been illustrated and described, it will be appreciated that various changes can be made therein without departing from the spirit and scope of the present invention.

We claim:

1. A suction catheter suitable for use in removing undesirable fluid from a patient, said suction catheter comprising:
   a catheter tube having a proximal end and a distal end;
   means for connecting the proximal end of said catheter tube to a vacuum source;
   an annular collar encircling said catheter tube and axially movable along said catheter tube and having an airtight wiper seal adjacent to the outer wall of said catheter tube;
   a crosspiece mounted so as to surround said catheter tube in the vicinity of the distal end of said catheter tube and having an opening for connection to a ventilator; and
   an indicator sleeve connected between said annular collar and said crosspiece, said indicator sleeve inflating and deflating as a patient respirates through said crosspiece so as to provide a visible indication of said respiration.

2. The suction catheter of claim 1 further comprising a lavage conduit extending longitudinally along said catheter tube for delivering lavage solution into the patient.

3. The suction catheter of claim 1 wherein said connecting means includes a manually operable normally closed valve.

4. The suction catheter of claim 3 further comprising a protective sleeve surrounding said catheter tube from said valve to said annular collar.

* * * * *